United States Patent [19]

Lee

[11] Patent Number: 4,790,325
[45] Date of Patent: Dec. 13, 1988

[54] AUTOMATIC ARTERIAL BLOOD PRESSURE RECORDER

[76] Inventor: Arnold S. Lee, 2008 Cotner Ave., Los Angeles, Calif. 90025

[21] Appl. No.: 74,363

[22] Filed: Jul. 16, 1987

Related U.S. Application Data

[62] Division of Ser. No. 801,248, Nov. 25, 1985.

[51] Int. Cl.$^4$ .............................................. A61B 5/02
[52] U.S. Cl. ..................................... 128/677; 128/686
[58] Field of Search ............... 128/660, 662, 677–679, 128/682, 683, 686, 900, 714, 802, 803, 639, 644

[56] References Cited

U.S. PATENT DOCUMENTS

| | | | |
|---|---|---|---|
| 1,857,567 | 5/1932 | Plesch | 128/686 |
| 2,149,690 | 3/1939 | Snyder | 128/900 |
| 2,693,794 | 11/1954 | Neville | 128/686 |
| 3,187,745 | 6/1965 | Baum et al. | 128/639 |
| 3,640,271 | 2/1972 | Horton | 128/662 |
| 3,757,772 | 9/1973 | Goldblat et al. | 128/686 |
| 3,935,984 | 2/1976 | Lichowsky et al. | 128/686 |
| 4,441,504 | 4/1984 | Peterson et al. | 128/677 |

FOREIGN PATENT DOCUMENTS

| | | | |
|---|---|---|---|
| 0033567 | 8/1981 | European Pat. Off. | 128/677 |
| 2837707 | 3/1980 | Fed. Rep. of Germany | 128/686 |

*Primary Examiner*—Max Hindenburg
*Attorney, Agent, or Firm*—Spensley Horn Jubas & Lubitz

[57] ABSTRACT

One aspect of the present invention involves a blood pressure recorder system of the type having an inflatable cuff, a pressurized gas source and an inflation valve. The system includes a cuff pressure trigger unit which senses the gas pressure in the cuff. When the duration of significant gas pressure in the cuff exceeds a predetermined time, the cuff pressure sensor facilitates relieving pressure in the cuff. The system also includes a safety system for insuring that the cuff pressure trigger unit is operative. The safety system is independent of changes in the input power.

Also disclosed is an improved doppler ultrasonic blood pressure transducer and a novel method for automatically positioning a blood pressure transducer adjacent a skin surface.

15 Claims, 4 Drawing Sheets

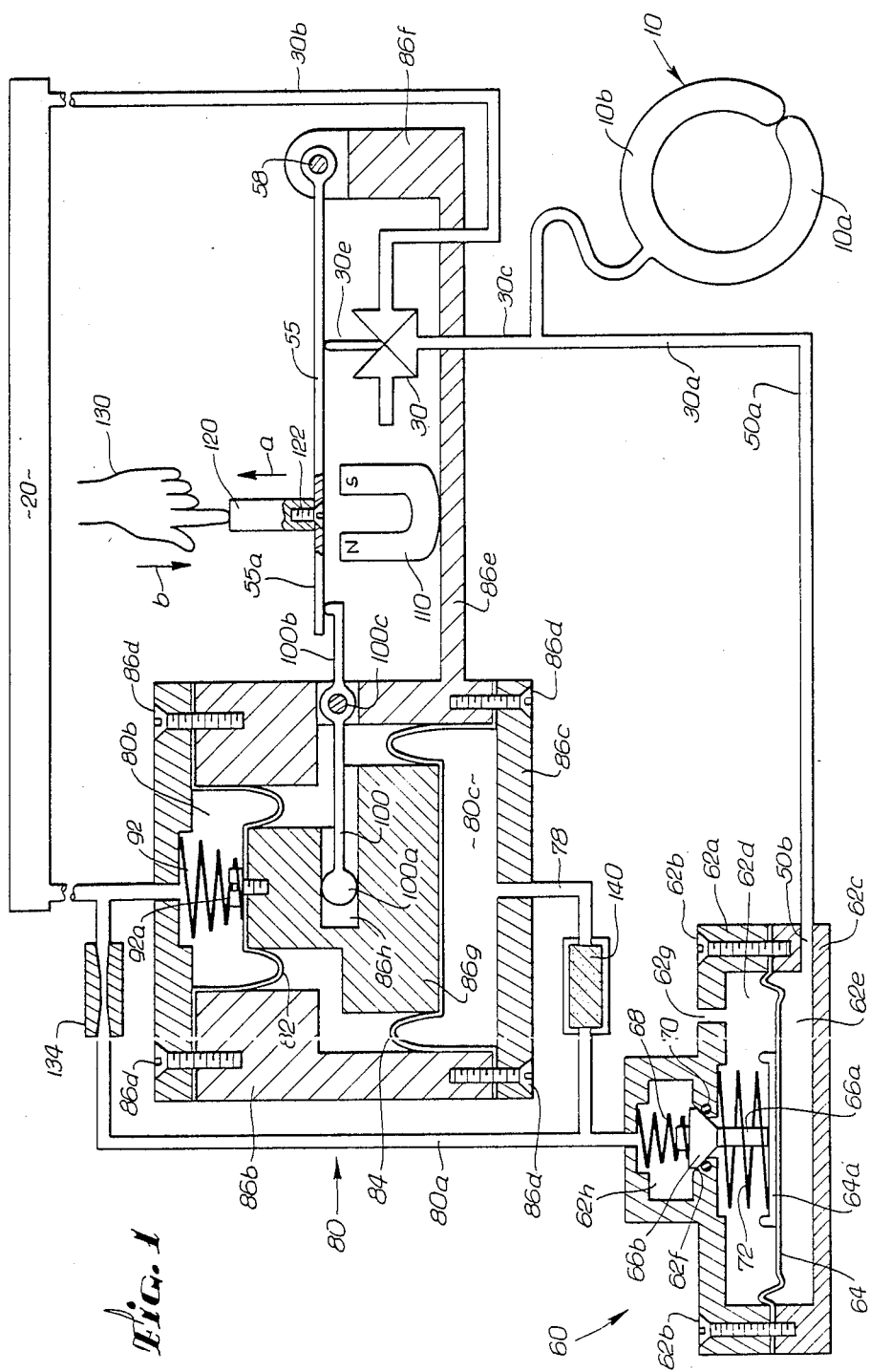

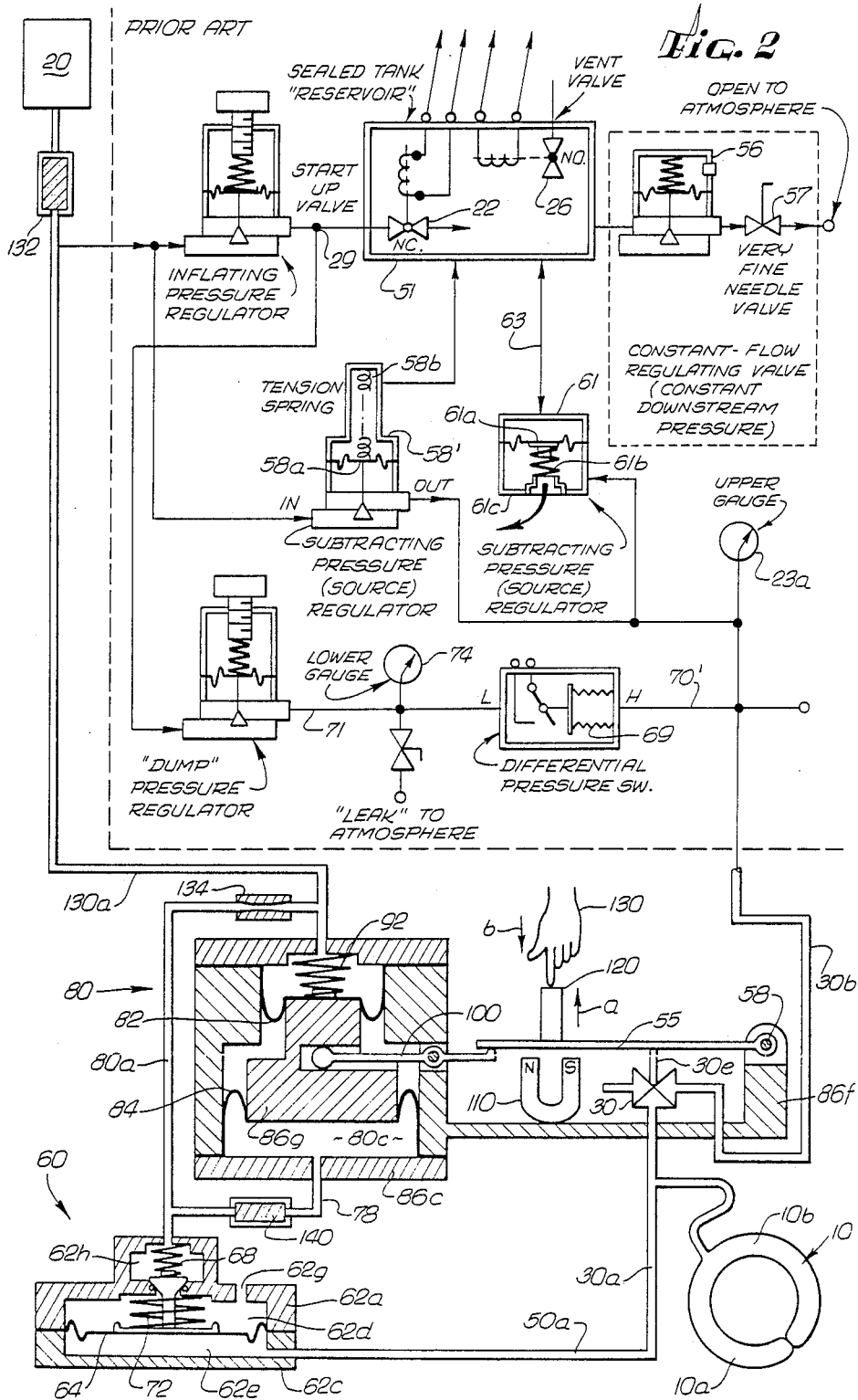

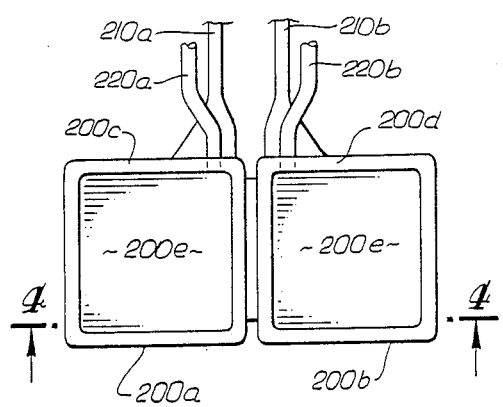
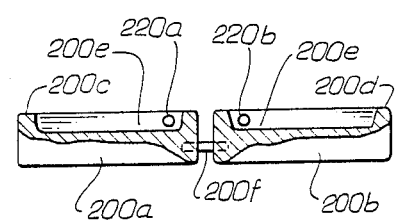
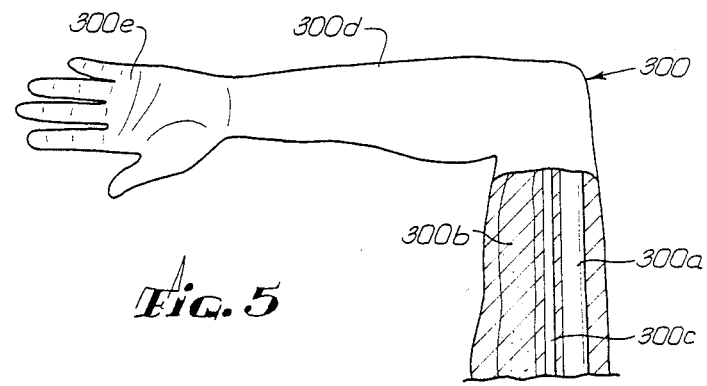
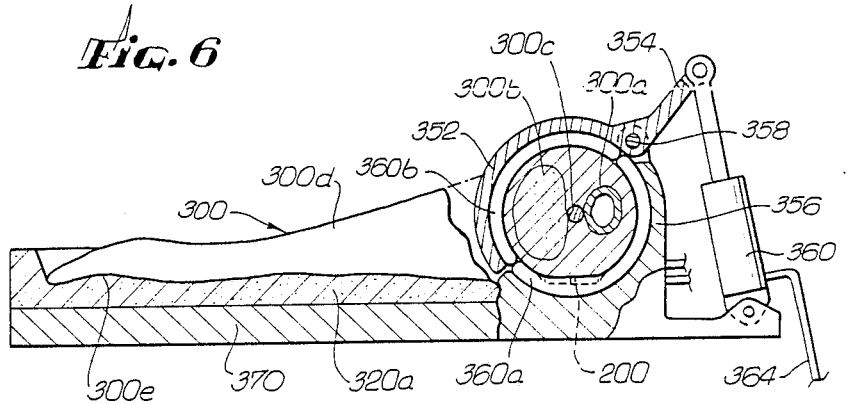

AUTOMATIC ARTERIAL BLOOD PRESSURE RECORDER

This is a division of application Ser. No. 801,248, filed on Nov. 25, 1985.

FIELD OF THE INVENTION

The present invention relates to the field of blood pressure recording systems. In particular, the present invention relates to a system for recording blood pressure wherein cuff pressure is automatically relieved if its duration or duty cycle exceeds a predetermined time. The present invention further relates to an improved ultrasonic arterial wall motion transducer and an improved method of coupling said ultrasonic transducer to a subject.

PRIOR ART

There are several impediments to the unattended use of an automatic blood pressure recorder having an inflatable cuff, for example, a recorder of the type generally exemplified by U.S. Pat. Nos. 4,027,662 and 4,069,815. If the recorder malfunctions and causes the cuff pressure to exceed the patient's blood pressure for too long a period, the patient could suffer irreparable damage. The damage caused by prolonged (about one hour in some cases) cuff inflation could well cause a complete loss of the limb. Such damage would be identical to a tourniquet being left on the arm for about an hour. In patients with defective circulation, far less time could result in harm. Even if the cuff is regularly deflated, if the proportion of time in inflation is more than about 35%, harm may result.

In modern automatic indirect arterial pressure instruments, the cycling of the cuff pressure is typically controlled by a combination of electric/electronic/pneumatic elements powered by line voltage, a rechargeable battery or compressed gas. The power source could break down, or supply the wrong power; a component of the system may not function. A safety system which will be reliable in protecting the subject in light of all possible combinations of malfunction and defective/deficient power has in the past been, and is presently, needed.

Any safety system which is triggered solely upon the malfunction of the protected apparatus may well not be used for years, after which length of time the safety system itself might be maloperative and therefore undependable. Thus it is necessary to continually test the safety system itself, even though such testing might be boring to, and easily disregarded by, the instrumentation operator.

The application of an ultra-sonic arterial wall motion transducer of the type shown in U.S. Pat. No. 3,527,197 to the arms, legs or other limbs traditionally has required a properly applied coupling "gel," actually water, thickened to prevent its leaking away, to avoid the impedance mismatch problems in ultrasonic wave transmission caused by the layer of air between the active surface of the transducer and the skin. Care must be exercised to properly apply the gel, and the transducer manufacturer recommends to make certain that no air bubbles are entrailed in the gel. The gel-detector-cuff application typically requires an attendant. Furthermore, the gel must be cleaned away after each use, as it leaves an undesirable residue upon evaporation.

The improvements to the automatic blood pressure system which constitutes the subject of the present invention overcome the above noted impediments, so that a patient, alone, can safely and expeditiously utilize an automatic, indirect, non-invasive blood pressure apparatus to obtain, and transmit to another location if desired, accurate, reliable systolic and diastolic pressure information.

ADVANTAGES OF THE PRESENT INVENTION

One aspect of the present invention is a blood pressure cuff safety system which performs the following functions:

(1) Each time compressed gas "power" is connected to the instrument an automatic test of the safety system occurs;

(2) Whenever pressure greater than approximately 20 Torr (0.4 psi) exists continually in the cuff for more than a few minutes, the cuff is automatically disconnected from the pressure source and connected to the atmosphere (pressure in the cuff is relieved), and an alarm signal can be given; and (3) If pressure cycling occurs so that pressure in the cuff is above 20 Torr for more than approximately 50% of the time for more than a few minutes, the cuff is similarly automatically connected to the atmosphere and an alarm signal can be given.

The safety system include no electrical/electronic elements; therefore no electrical power is required. All elements are mechanical and pneumatic (a permanent magnet is included). No pneumatic pressure source is required to put the system into the disconnect-cuff-and-alarm mode so that lost pressure will not affect the safety system's integrity. Furthermore, the safety system is completely independent from the operational system of the blood pressure apparatus.

DESCRIPTION OF THE DRAWINGS

FIG. 1 is a schematic diagram of the safety system of the present invention.

FIG. 2 is a schematic diagram of the safety system of the present invention connected to a prior art blood pressure recorder, the prior art portion shown to the right of, and above, the dashed line.

FIG. 3 is a top view of the improved transducer of the present invention showing the transducer active surface.

FIG. 4 is a side view of the improved transducer of the present invention taken along line 3—3 of FIG. 3.

FIG. 5 shows a cut-away of the bottom of an arm used as a test portion in conjunction with the improved transducer of the present invention.

FIG. 6 is a cross-sectional view of the automatic blood pressure cuff system of the present invention.

SUMMARY OF THE INVENTION

Figure 7:
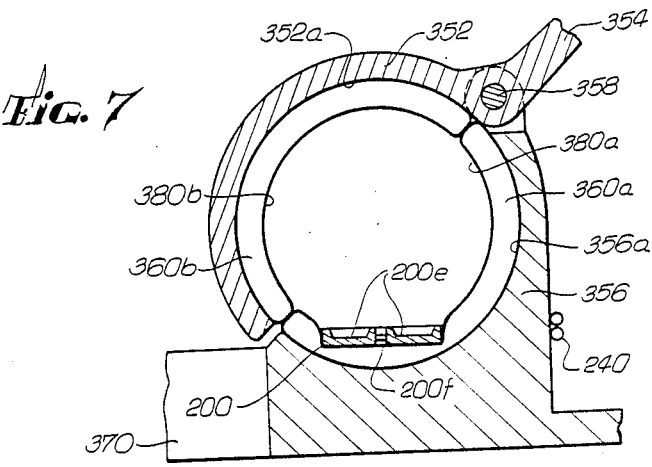
FIG. 7 is a cross-sectional view of a portion of the automatic blood pressure cuff system of the present invention.

One aspect of the present invention involves a blood pressure recorder system of the type having an inflatable cuff, a pressurized gas source and an inflation valve. The system includes a cuff pressure trigger unit which senses the gas pressure in the cuff. When the duration of significant gas pressure in the cuff exceeds a predetermined time, or when the duty cycle exceeds a predetermined value, the cuff pressure trigger unit facilitates disconnecting the cuff from the cuff pressure source and relieving pressure in the cuff.

The system also includes a safety system for insuring that the trigger unit is operative. The safety system includes a force-differential-sensor which preferably comprises a cylinder having two chambers, with the chambers having different-effective-area-pressure-responsive diaphragms, operating upon the same floating piston, moveable in response to movement of the diaphragms and operatively coupled to the 3-way cuff valve. One chamber, containing the smaller effective area diaphragm is connected directly to the system inlet pressurized gas source, and the other chamber is connected with a flow restrictor to the same system inlet pressurized gas source.

The piston is positioned between the diaphragms so that the 3-way cuff valve is not actuated (cuff connected only to atmosphere) when the pressurized gas source is initially coupled to the system. However after a certain period of time, the chamber having the flow restricted connection is pressurized thereby moving the piston to a position whereby the 3-way cuff valve is actuated (cuff may receive pressure). If the pressure exceeds a predetermined excess pressure value for a predetermined time, the cuff pressure trigger unit operates upon the force-differential-sensor to relieve the pressure in the chamber having the input flow restricted thereby re-positioning the piston so that the 3-way cuff valve is deactuated to relieve the pressure in the cuff. The safety system is independent of changes in the input power.

Another aspect of the present invention involves an improved transducer of the type having an active surface which is pressed against a test portion of a patient's skin when the transducer is operated. The improvement comprises means, connected to the transducer, for receiving and retaining a coupling fluid such as pure water, between a portion of the transducer active surface and the test portion of the patient's skin, to minimize impedence mismatch. The improvement further includes means for automatically delivering the coupling fluid to the receiving and retaining means. These aspects of the present invention avoid use of a messy gel, and when used with other elements of the present invention as described above and below, facilitates automating blood pressure recordation.

Another aspect of the present invention is concerned with an automatic blood pressure recordation system comprising a transducer connected to the inner surface of a blood pressure cuff, a mold having a depression of at least a portion of the body adjacent to the test portion of the body to be connected to the cuff during operation of the transducer, and means for automatically bringing the cuff and transducer into operational contact with the test portion. This aspect of the present invention facilitates use of an automatic blood pressure apparatus by a patient without an attendant, without training, without operational details, and with only the minimal collaboration by the patient, i.e., sitting in a chair, and placing an arm on a special armrest equipped with a clam shell-type blood pressure cuff having the ultrasonic doppler transducer according to this invention mounted on its inner surface.

DETAILED DESCRIPTION OF THE INVENTION

The following description is the best presently contemplated made of carrying out the invention This description is made for the purpose of illustrating the general principles of the invention and is not to be taken in a limiting sense The scope of the invention is best determined by reference to the appended claims.

Referring to FIGS. 1 and 2, one embodiment of the blood pressure recorder system of the present invention (FIG. 1) is shown connected to a blood pressure recorder system (above and to the right of the dashed lines in FIG. 2) of the type disclosed in U.S. Pat. Nos. 4,027,662 and 4,069,815 (FIG. 2), which patents by this reference are incorporated verbatim herein.

The blood pressure recorder system of the present invention is of the type having an inflatable cuff 10, a pressurized gas source 20, and a 3-way cuff valve 30. The inflatable cuff 10 is an elastic, flexible cuff which can include upper and lower rubber bladders 10a,b, which can encircle the arm, leg or other portion of the subject patient and be positioned adjacent the test portion of the patient's skin. The cuff 10 is connected (in flow communication) by suitable linkage 10c to valve outlet tube 30a, one end of the valve outlet tube being connected to valve 30 and the other end of the valve outlet tube being connected to cuff pressure sensor linkage 50a, which is in turn connected to cuff pressure trigger unit 60.

The valve 30 has a valve input tube 30b through which the pressurized gas flows from an inflating-deflating pneumatic system (such as that shown in FIG. 2), an outlet 30c to the cuff and an outlet 30d open to the atmosphere. The valve 30 is preferably a common three-way valve, having a push down-spring up actuator 30e which selectively allows gas from the tube 10c to flow either to the atmosphere outlet tube 30d or allows gas from the tube 30b to flow from the outlet tube 30c to the cuff. Such a valve actuator 30e is operated using iron lever 55 which moves up and down in the direction of arrows "a" and "b", respectively, thereby to selectively move or push in the valve actuator 30e. Operation of the iron lever 55 is discussed in further detail below.

Cuff pressure trigger unit line 30a leads to aperture 50b in cuff pressure trigger unit 60. Cuff pressure trigger unit 60 is similar to a low pressure pneumatic or piloted valve or "switch. " That is, when sufficient pressure to overcome springs 68 and 72 passes through the cuff pressure trigger unit line 30a, valve stem 66a and valve 66b move up thereby allowing gas to flow from upper chamber 62h to middle chamber 62d and through aperture 62g open to the atmosphere as more fully discussed below. Thus, when the cuff pressure exceeds a predetermined pressure, for example 20 Torr, for a predetermined time, the cuff 10 will be automatically disconnected from the cuff pressure source and deflated as discussed in detail below.

The cuff pressure trigger unit 60 preferably comprises an upper casing 62a connected by screws 62b to lower casing plate 62c. A flexible diaphragm 64 supporting plate diaphragm 64a moves in response to changes in pressure between middle chamber 62d and lower chamber 62e. Cuff pressure sensor line 30a is in flow communication with lower pressure chamber 62e.

The cuff pressure trigger unit further includes valve 66b biased downwards by spring 72. The spring 72 is sufficient to exert a force on the diaphragm 64 such that it takes the predetermined pressure (e.g., 20 Torr) in cuff pressure sensor line 30a to open valve 66b. Preferably, the spring 72 exerts a force so that it takes about 20 Torr (mm Hg) to open the valve 66b.

The valve 66b includes valve stem 66a pushing against plate 64a and having a valve head capable of being forced against "O" rings 70 which are positioned in valve seat 62f. A light compression spring 68 biases the valve 66b into a closed and sealed position (not shown).

The upper casing 62a includes aperture 62g which allows flow communication from the middle chamber 62d to the atmosphere. In operation then, if the pressure in the lower chamber 62e remains below the predetermined pressure, the valve 66b will remain closed, i.e., the valve head 66b will fit snugly in the valve seat 62f. However, if the pressure in the cuff pressure trigger unit line 30a exceeds the predetermined pressure, the diaphragm 64 will move upward thereby opening the valve 66b allowing the atmosphere to communicate via the aperture 62g with the upper and middle chambers 62d and 62h, respectively, the latter of which communicates with safety unit vent line 80a.

In flow communication with upper chamber 62h, via force-differential-sensor vent line 80a, is force-differential-sensor unit 80. In general, force-differential-sensor unit 80 is a means for timing the actuation of the 3-way cuff valve 30 in response to a gradually varying pressure differential.

Force-differential-sensor unit 80 includes a force differential sensor having two chambers 80b,c, with each chamber having a pressure-responsive member or diaphragm 82, 84. Preferably the pressure-responsive members are belloframs of different area as explained in detail below. The force-differential-sensor unit 80 includes upper casing plate 86a and lower casing plate 86c connected by screws 86d to cylindrical plate 86b. A lower portion of the cylindrical plate 86b includes arm 86e having upstanding portion 86f pivotally connected by pin means 58 to iron lever 55. A lightweight, preferably plastic, floating piston 86g is enclosed within the valve casing 86a,b,c, and is supported by upper and lower belloframs 82,84 having effective areas A1 and A2, respectively The exposed area of the belloframs 82,84, and the exposed inner surface of the upper and lower valve casing plates 86a,c therefore define two enclosed chambers, namely upper chamber 80b and lower chamber 80c. A compression spring 92, located by screw head 92a on upper diaphragm 82 and floating piston 86g, biases the piston 86g towards the lower valve casing plate 86c. The space defined by the lower surface of diaphragm 82, and the upper surface of diaphragm 84 is open to atmosphere.

The floating piston 86g includes aperture 86h for holding end 100a of rocker arm 100 so that movement of end 100a within the aperture 86h is restrained. The other end 100b of rocker arm 100 extends outside of the valve casing, and contacts the end 55a of iron lever 55. When the piston 86g moves upward, the rocker arm 100 pivots about the pin means 100c thereby moving the end 100a up and thus the end 100b down. When the force exerted by diaphragm 82 on piston 86g is greater than the force exerted by diaphragm 84, the piston 86g moves in the opposite direction thereby pivoting the rocker arm 100 also oppositely and thereby causing the rocker to pivot to cause the iron lever 55 to move away from permanent magnet 110. Since the attraction of the magnet 110 for iron lever 55 is much greater when the two are actually in contact, once the iron lever moves the slightest distance away from the magnet, the lever quickly "flies away" completely The iron lever 55 also includes buttom 120 connected by screw 122. Hand 130 pushing with sufficient force in the direction of the arrow "b" upon button 120 can move the iron lever 55 into contact with the permanent magnet 110, while pivoting the rocker arm 100 and actuating three-way valve 30.

Casing aperture 86i is connected by tube 130a to suitable filter 132, and the other elements of a blood pressure system (shown within the dashed lines in FIG. 2), which are connected to system inlet pressure source 20 which pressure may be in the range of zero to sixty pounds per square inch although the operational pressure range is preferably 30 to 60 psi.

In communication with the outflow line 130a is lower resistance flow restrictor 134, preferably restricting the flow of gas from tube 130a to tube 80a to 25 cc's per minute at 30 psi differential. The vent line 80a directs the flow of gas from the lower resistance flow restrictor 134, and is in flow communication both with the cuff pressure trigger unit aperture 70 and higher resistance flow restrictor 140 which preferably restricts the flow of gas from tube 80a to tube 78 to about 5 cc's per minute at 30 psi differential. Gas can flow through the linkage 78 from the higher resistance flow restrictor 140 to the chamber 80c. Thus, pressurized gas from the pressure source 20 is connected directly from the pressurized gas source 20 to chamber 80b and is flow-restricted to chamber 80c.

In a preferred embodiment, the effective area of chamber diaphragm 84, A1, is 2.7 times the effective area of chamber diaphragm 82, A2. Pressure P2 in chamber 80b acts upon A2. A downward force F2 which is equal to P2 multiplied by A2 is exerted on the floating piston 86g. Pressure P1 in chamber 80c acts upon A1 and produces an upward force F1 equal to pressure P1 multiplied by area A1. The forces on the piston 86g are balanced when force F1 equals force F2. Since area A1 equals 2.7 multiplied by area A2, at balance, P1 equals 0.37 P2. Thus, P1 must be maintained greater than approximately 0.4 P2 to maintain contact between the iron level 55 and the magnet 110 without pushing the button 120. The relatively small force of biasing spring 92 adds slightly to the force equal to the product of P2 and A2.

It should be appreciated that the higher resistance flow restrictor 140 preferably passes 5 cc's of gas per minute at a 30 psi pressure differential. The preferable resistance of the higher resistance flow restrictor 140 is thus approximately 6 psi per cc per minute. Equally so, the resistance of the lower resistance flow restrictor 134 is approximately 1.2 psi per cc per minute. Of course other restriction parameters are within the scope of the present invention and are chosen depending upon the particular construction of the safety system of the present invention as well as the cuff threshold pressure.

The operation of the safety system will now be described. Initially, with the compressed gas source 20 having been disconnected or shut off for more than approximately 10 minutes, the piston spring 92 produces more force [than the attraction of the magnet 110 for the iron lever (when the iron lever is pushed against the magnet)] pushing piston 86g down and thus moving iron lever 55 away from permanent magnet 110. Thus, when hand 130 pushes plastic button 120, hence pushing the iron lever 55 against the magnet 110, the iron lever 55 will not attach itself or be captured by the magnet 110, but springs back when the hand 130 stops pushing.

The iron lever 55 can contact or press against the actuator 30e of the valve 30. When the iron lever 55 is tight against the magnet 110, the valve 30 allows compressed gas from the cuff inflating system to communicate with the cuff 10 thereby inflating the cuff. However, when the iron lever 55 is away from the magnet 110, the valve 30 disconnects the cuff 10 from the cuff inflating system and deflates cuff 10 by opening it to the atmosphere through line 30d. Thus, in the initial condition, the cuff 10 is deflated, and cannot receive compressed gas from anywhere.

When a compressed gas source is connected to the system, pressurized gas from the gas source is directed through the inlet lines 130a,b. The gas flowing through line 130a flows from suitable filter 132 directly to upper chamber 80b which immediately receives the full supply pressure, while chamber 80c receives compressed air slowly through low and high resistance flow restrictors 134, 140. Preferably, it takes about two minutes longer to fill chamber 80c then 80b. The floating piston 86g is pushed downward (direction "b"), as a result, causing the rocker arm 100 to exert a substantial force on the iron lever 55 to keep it from being captured by the magnet 110 unless the plastic button 120 is forcefully depressed. Thus during this, preferably, two minute period, release of pressure on button 120 by hand 130 allows lever 55 to spring up and away from magnet 110 thereby keeping the cuff 10 from being inflated It is only if button 120 is maintained by hand 130 in a depressed mode that cuff 10 could be inflated After about two minutes, enough pressure is built up in chamber 80c to overcome the combined forces of the piston spring 92 and the pressure on the piston 86g from the chamber 80b to move the piston 86g up, freeing the iron lever 55 to be captured by the magnet 110 when the plastic button 120 is pushed. Once this occurs, the lever 55 will remain captured by magnet 120 without further depression by hand 130. The length of time to reach this stage is approximately independent of the system inlet 130a pressure, since the fixed ratio of the chamber 80c piston/belloframe area to that of the chamber 80b piston/belloframe area is about 2.5 to 1,and the approximate linearity of restrictors form a timing circuit with the chamber 80c volume Any time after the approximate two-minute delay, pushing upon the plastic button 120 [which normally protrudes from a control panel (not shown)] until the iron lever 55 touches the magnet 110, allows the magnet 110 to capture the lever 55 and thus maintain the valve 30 in the actuated state, i.e., the cuff 10 is flow connected to its pressurizing and depressurizing system. The combination of the initial refusal by the valve 30 to pressurize the cuff 10, and the subsequent turning on of the cuff pressure, constitutes a complete proof that the safety system of the present invention is in proper operating condition.

In normal operation, each time the cuff 10 is inflated to a pressure greater than about 20 Torr, valve 66b opens and gas is free to leak out of the chamber 80c through the high resistance flow restrictor 140 into upper chamber 62h. The usual cuff pressure portion of the operational cycle is about 25 seconds Because of the resistance of the high resistance flow restrictor 140, the pressure in chamber 80c will not fall sufficiently during that short period of time to allow the piston 86g to move downward. Subsequent fall in cuff pressure below 20 Torr allows the valve 66 to close, and chamber 80c is refilled through the low resistance flow restrictor 134. Thus the system remains operative during normal cyclical use.

If unrelieved pressure above about 20 Torr remains in cuff 10 for more than about 2 minutes, the pressure in chamber 80c will fall as discussed in the prior paragraph. The piston spring 92 and the pressure in chamber 80b will push piston 86g down and cause the iron lever 55 to be pushed off the magnet 110, and the valve 30 to be returned to its normal (deactuated) state, i.e., the cuff 10 is disconnected from its pressure source, and connected to the atmosphere and therefore deflated. Too frequent cycling also will allow the chamber 80c pressure to fall and cause the piston 86g to move downward, pushing the lever 55 off the magnet 110. Thus, too high duty-cycle pressure cycling also triggers the safety system. In such cases, the plastic button will have to be pushed again to reactivate the system.

Thus, in summary, the safety system of the present invention includes:

(1) means for conditionally connecting the blood pressure cuff either to its operational source of pressurizing and depressurizing or to atmosphere, (2) means responsive to the duration of significant cuff pressurization and to the duty cycle of cuff pressurization operative upon means (1), (3) means responsive to the time period after initial application of the compressed air "power" operative upon means (1), and (4) means responsive to the cuff pressure, such means acting as a trigger whenever cuff pressure is significant; i.e., above some predetermined low pressure, which trigger operates upon means (2).

It should be appreciated that use of the terms upper and lower are for illustrative purposes only. It should also be appreciated that there are a variety of modifications of this aspect of the present invention.

A second problem solved by the present invention is the construction of an automatic blood pressure apparatus which is usable by a patient without an attendant, without training, without operational details and with only the minimal collaboration by the patient. The problem is solved by a subject patient sitting in a chair, placing an arm on a special armrest equipped with an automatic clam shell type blood pressure cuff having an improved ultrasonic doppler transducer mounted on its inner surface.

The improved transducer of the present invention concerns improvement in transducers of the type having an active surface coupled to a test portion of a subject, and permits the use of a non-thickened coupling fluid such as pure water. The required small amount of water is applied each time a clam shell-significant shaped cuff is closed upon, for example, the portion of the arm containing the brachial artery. The transducer is connected to the cuff and is positioned adjacent the brachial artery. The coupling liquid is retained in the space between the transducer active surface and the surface skin adjacent the artery by the combination of a special structure and a novel mode of operation In particular, the active surface of the transducer includes a slightly protruding rim of preferably very soft material, such as pure silicon rubber, forming a well. The rim is pierced by a miniscule plastic flexible tube for the water injection, and is pressed against the skin test portion by the weight of the arm in addition to the force from the pressurized cuff. Injection of a coupling fluid such as pure water through the tube into the well is by means known in the art such as automatic injectors and even a syringe.

Preferably, the patient's arm rests upon a special armrest, preadjusted to the patient's height, so that the arm extends horizontally from the shoulder in the frontal plane, with the forearm bent at 90°, extending forward, palm down, also resting upon the special armrest. The armrest has affixed to it a cuff with a transducer connected to it in the proper place for the particular patient and means for automatically coupling the cuff to the test portion so that the test portion is adjacent the transducer. The special armrest preferably has confining channels so that the arm or test portion of the patient is repeatedly constrained to the identical position with respect to the cuff and the transducer each time the arm is inserted into the cuff. In such a relationship, the brachial artery may be perfectly spaced in relation to the transducer, without any judgmental decisions on the part of the patient.

With specific reference to FIGS. 3 and 4, the improved transducer of the present invention is shown. The transducer includes active surfaces 200a,b to which are connected wires 210a,b which are in turn connected to ultrasonic crystals (not shown). A hinge 200f holds the two active surfaces together, although one or more than two active surfaces are within the scope of the present invention. Preferably surrounding the active surfaces are two rims 200c,d, preferably comprising pure silicon rubber. Each rim 200c,d forms a depression or a well 200e for receiving and retaining a coupling fluid, for example, preferably a non-thickened fluid such as pure water. Miniscule plastic flexible tubes 220a,b are pierced through the rim and are at one end connected to a coupling fluid injection means 230 for injecting the coupling fluid into the wells 200e. The other end of the tubes 200a,b flow communicates with the wells. Therefore, when the coupling fluid is injected through the tubes 220a,b, the coupling fluid is received and retained by the wells 200e. Thus, when an arm or leg of a subject is pressed against an active surface having a rim, the rim forms a seal between the active surface and the skin test portion thereby eliminating the problem of using thick, messy gels to correct impedence mismatch.

It is often not possible to completely seal the rim to the skin test portion because of hair and skin irregularities. Thus, the present invention envisages the well formed by the rim and the transducer to be spacially horizontal, so that the water has little driving force to escape from the well.

With the above in mind, and with further reference to FIGS. 5-9, one embodiment of an improved automatic blood pressure system of the present invention is shown. FIG. 5 shows a cutaway of the bottom of an arm 300 used as a test portion. There is shown humerus bone 300a, muscle 300b (biceps mostly) and brachial artery 300c. It is brachial artery 300c that is placed adjacent to the active surface of a transducer in the armrest of the present invention by using a clam shell type blood pressure cuff of the present invention as discussed below. The clam shell cuff is well known in the art.

FIG. 6 shows arm 300 in place within the clam shell cuff, with the forearm 300d bent at 90°, extending forward, palm 300e down. A special armrest 370 is built in the armrest of a chair (not shown) and includes an arm positioning guide 320a which is formed around the lower portion of the forearm 300d having an exact depression of the bottom of the forearm, palm and fingers. Also shown is the clam shell means for automatically bringing the cuff bladders 360a,b (may be a single or a dual bladder) and the transducer 200 into operational contact with the test portion of the patient adjacent the brachial artery.

With reference also to FIG. 7, the means for automatically bringing the cuff and transducer into operational contact with the test portion of the patent includes upper clam shell half 352 (which is connected, preferably integrally, to clam shell operating lever 354) and lower clam shell half 356 which is pivotally connected by hinge 358 to upper shell operating lever 354. Clam shell operating lever 354 is connected to compressed air cylinder 360 having a spring return. A compressed air hose 364 from the compressed air cylinder 360 is shown leading to a compressed air source (not shown). As shown, the transducer 200 is positioned so that well 200e is facing the test portion of the arm of the patient, and is horizontal with the well opening up.

The physical interaction between the cuff, transducer and the clam shell is shown in further detail in FIG. 7. FIG. 7 shows special armrest 370 connected to lower clam shell 356, preferably integral therewith. Affixed to the inner surface 356a of lower clam shell 356 is lower rubber bladder 360a or lower portion of the single bladder (having outer surface 380a) which is a portion of inflatable cuff 360. Affixed to the inner surface 352a of upper clam shell 352 is upper rubber bladder 360b, the upper rubber bladder having an outer surface 380b. Ultrasonic transducer 200 is connected to the outer surface 380a of lower rubber bladder, and is positioned so that when the arm is clamped in the shell, the transducer active surface (and wells 200e) are positioned adjacent brachial artery 300c, and horizontal with active surface facing upward.

In the embodiment shown in FIGS. 6 and 7, the clam shells 352 and 356 are shown in a closed or clamped state, that is, with the cylinder 360 pressurized. When the cylinder 360 is depressurized, the cylinder is allowed to spring the upper clam shell 352 open due to a return spring (not shown). Thus the arm can be easily removed from the clam shells With reference again to FIG. 7, it should be appreciated that a small space is shown below the bladders and their adjacent neighbors. This is due to the limitations of illustration only, actually, pressure in the bladder causes its walls to intimately press against whatever it contacts It should be further appreciated that the coupling fluid is retained in the transducer depression or well 200e partly because a patient's skin seals to the soft rim 200c,d of the transducer and because the horizontal position of the transducer keeps the coupling fluid in its well even though the seals may not be perfect (because of hair and other irregularities). Furthermore, the coupling fluid cannot exit through the filling tubes 220a,b because the tubes lead to a completely filled chamber of the injection means 230.

Figure 8:
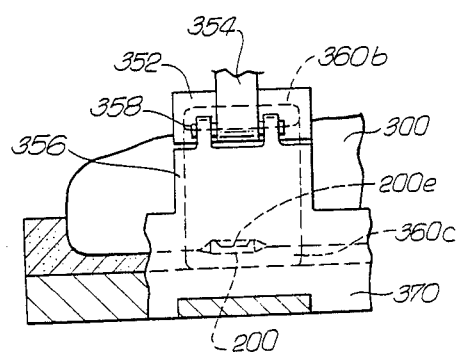
FIG. 8 is a rear view (partially cutaway) of the means for automatically bringing a transducer such as that of the present invention into operational contact with the test portion of the subject.

With reference to FIG. 8, a rear view of the clam shell is shown in a closed position, with a flexible, easily distensible rubber bladder bag 360a,b filled in phantom.

Figure 9:
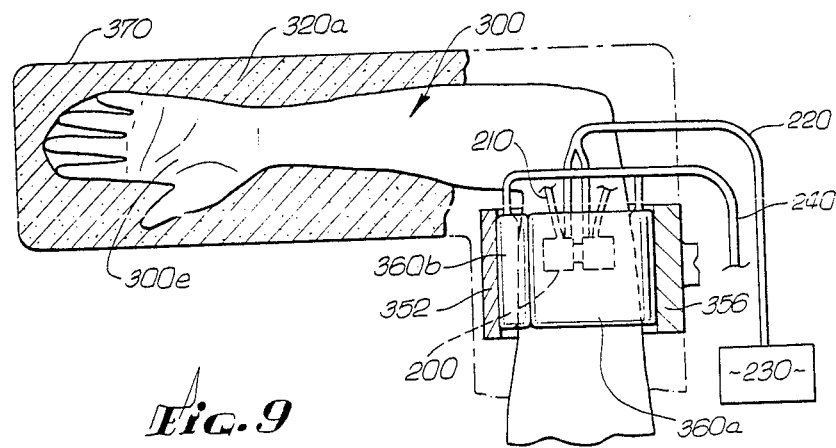
FIG. 9 is a bottom view of the means for automatically bringing a transducer into operational contact with the test portion of the subject.

FIG. 9 shows a bottom view with the tubes and wires from the transducer and the well leading to ultrasonic crystals (now shown) and injection means 230, respectfully, and tubes 240 leading to a compressed air source (not shown) from the cuff bladder bags.

I claim:

1. A device for facilitating the measurement of blood pressure in the brachial artery of an arm of a test subject, said system including:

a transducer of the type for estimating blood pressure, the transducer having an active surface, a rim connected to the transducer and substantially surrounding the active surface, and means for supplying a coupling fluid to the partially enclosed space defined by the rim and active surface; and means for supporting the transducer in a substantially horizontal position such that when the rim is in intimate contact with the arm, and the active surface is in close proximity to the skin adjacent to the brachial artery, a liquid located in the partially enclosed space remains in said partially enclosed space;

wherein the liquid couples the active surface of the transducer to the skin adjacent to the brachial artery and wherein said liquid is in operable contact with both the active surface of the transducer and the arm of the test subject.

2. The device of claim 1 wherein the liquid is non-thickened.

3. The device of claim 2 wherein the liquid is completely evaporatable.

4. The device of claim 1 wherein the coupling fluid is water.

5. The device of claim 1 wherein the means for supporting the transducer in a substantially horizontal position includes an arm rest.

6. The device of claim 1 wherein the transducer is an ultrasonic transducer.

7. The device of claim 5 wherein the arm rest is adapted to support the arm of the test subject in a generally horizontal plane so that the arm extends horizontally from the shoulder.

8. The device of claim 7 wherein the arm rest further includes a confining channel adapted to matingly receive the portion of the arm of the test subject which contains a portion of the brachial artery.

9. The device of claim 1 further including a cuff for restricting the flow of blood in the arm of the test subject.

10. The device of claim 9 wherein the cuff includes first and second halves movably connected to one another.

11. The device of claim 5 wherein the means for supporting the transducer in a substantially horizontal position includes a clam shell cuff.

12. The device of claim 11 wherein the clam shell cuff is attached to the arm rest.

13. A method for estimating the blood pressure in a test subject, the method comprising the following steps:

providing a transducer of the type for estimating blood pressure, the transducer having an active surface, a rim connected to the transducer and substantially surrounding the active surface, and means for supplying a non-thickened, completely evaporatable coupling fluid to a partially enclosed space defined by the rim and active surface;

supporting the transducer in a substantially horizontal position such that when the rim is in intimate contact with the arm, and the active surface is in close proximity to the skin adjacent to the brachial artery, coupling fluid located in the partially enclosed space remains in said space;

bringing the rim of the transducer into intimate contact with the arm such that the non-thickened liquid functions as a coupling fluid between the active surface of the transducer and the arm, wherein said liquid is in operable contact with both the active surface of the transducer and the arm of the test subject;

providing a cuff for restricting the flow of blood in the arm of the test subject; and estimating the blood pressure of the test subject by restricting the flow of blood in the arm and gradually releasing the restriction to blood flow.

14. The method of claim 13 wherein the transducer is supported in a substantially horizontal position by an arm rest adapted to support the arm of the test subject in a generally horizontal plane so that the arm extends horizontally from a shoulder.

15. The method of claim 13 wherein the cuff comprises a clam shell cuff having first and second halves movably connected to one another.

* * * * *